United States Patent
Cavazos Sepulveda et al.

(10) Patent No.: US 12,181,406 B2
(45) Date of Patent: Dec. 31, 2024

(54) CONTACTLESS MEASUREMENT OF ROCK WETTABILITY BY PHOTONIC TECHNIQUES

(71) Applicant: Saudi Arabian Oil Company, Dhahran (SA)

(72) Inventors: Adrian Cesar Cavazos Sepulveda, Nuevo Leon (MX); Damian Pablo San Roman Alerigi, Al-Khobar (SA); Ziyad K. Kaidar, Dhahran (SA); Thamer Zahrani, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 190 days.

(21) Appl. No.: 18/082,186

(22) Filed: Dec. 15, 2022

(65) Prior Publication Data
US 2024/0201079 A1 Jun. 20, 2024

(51) Int. Cl.
G01N 21/35 (2014.01)
G01N 21/3563 (2014.01)
(Continued)

(52) U.S. Cl.
CPC ..... G01N 21/3563 (2013.01); G01N 21/3581 (2013.01); G01N 21/552 (2013.01); *G01N 2201/1296* (2013.01)

(58) Field of Classification Search
CPC ........... G01N 21/3563; G01N 21/3581; G01N 21/552
See application file for complete search history.

(56) References Cited

U.S. PATENT DOCUMENTS

| 11,733,141 B1 * | 8/2023 | Liu | G01N 13/00 73/64.52 |
| 2004/0099804 A1 * | 5/2004 | Liu | G01N 21/64 250/301 |

(Continued)

FOREIGN PATENT DOCUMENTS

GB 2217838 11/1989

OTHER PUBLICATIONS

Joonaki et al., Water versus Asphaltenes; Liquid-Liquid and Solid-Liquid Molecular Interactions Unravel the Mechanisms behind an Improved Oil Recovery Methodology, Scientific Reports, www.nature.com/scientificreports, https://doi.org/10.1038/s41598-019-47782-5 (Year: 2019).*

(Continued)

Primary Examiner — Hugh Maupin
(74) Attorney, Agent, or Firm — Fish & Richardson P.C.

(57) ABSTRACT

Systems and methods include a computer-implemented method for analyzing rock samples. Rock and oil electromagnetic baselines are determined for rock samples in at least a section of an electromagnetic spectrum ranging from ultraviolet to long terahertz radiation. An aging process is conducted on each rock sample, initially starting with the rock and oil electromagnetic baselines. The aging process is repeated using spectrometry on the rock sample and measured wettabilities of the rock sample until changes in spectra are less than a predetermined threshold. Aging information including the spectra and wettabilities are stored in a machine learning database. Spectra are obtained from an unknown rock sample. The spectra are mapped to clusters in the machine learning database. Wettability ranges are determined for the unknown rock sample based on a mapping of the spectra of the unknown rock sample to clusters in the machine learning database.

20 Claims, 7 Drawing Sheets

(51) Int. Cl.
*G01N 21/3581* (2014.01)
*G01N 21/552* (2014.01)

(56) References Cited

U.S. PATENT DOCUMENTS

| | | | | |
|---|---|---|---|---|
| 2013/0125630 A1* | 5/2013 | Collins | ................... | E21B 43/20 |
| | | | | 73/64.56 |
| 2013/0161502 A1* | 6/2013 | Pomerantz | ......... | G01N 33/2823 |
| | | | | 378/53 |
| 2015/0153470 A1* | 6/2015 | Stove | ........................ | G01V 3/18 |
| | | | | 702/6 |
| 2015/0323517 A1 | 11/2015 | Washburn | | |
| 2017/0030819 A1* | 2/2017 | Mccarty | ................... | E21B 43/26 |
| 2019/0087939 A1 | 3/2019 | Hakimuddin | | |
| 2020/0096429 A1* | 3/2020 | Andersen | ................ | G01N 13/02 |
| 2020/0371051 A1 | 11/2020 | Chen et al. | | |
| 2020/0408090 A1* | 12/2020 | Kadayam Viswanathan | ................ | |
| | | | | E21B 49/02 |
| 2022/0283138 A1 | 9/2022 | Smith | | |

OTHER PUBLICATIONS

Al-Mahrooqi et al., "Wettability Alteration During Aging: The Application of NMR to Monitor Fluid Redistribution," International Symposium of the Society of Core Analysts, Toronto, Canada, Aug. 21-25, 2005, 12 pages.

Gómora-Herrera et al., "Study of Surface Wettability Change of Unconsolidated Sand Using Diffuse Reflectance Infrared Fourier Transform Spectroscopy and Thermogravimetric Analysis," Applied Spectroscopy, 2018, 72(4): 562-572, 11 pages.

International Search Report and Written Opinion in International Appln. No. PCT/US2023/084081, mailed on Apr. 9, 2024, 17 pages.

Taheri-Shakib et al., "The study of influence of electromagnetic waves on the wettability alteration of oil-wet calcite: Imprints in surface properties," Journal of Petroleum Science and Engineering, Sep. 2018, 168, 8 pages.

* cited by examiner

CONTACTLESS MEASUREMENT OF ROCK WETTABILITY BY PHOTONIC TECHNIQUES

TECHNICAL FIELD

The present disclosure applies to geology and determining information from rock samples, e.g., in the oil industry.

BACKGROUND

Infrared spectroscopy (or vibrational spectroscopy) is typically used to probe the molecular bonds directly using infrared (IR) electromagnetic waves. The spectral range of IR extends from 800 nanometers (nm) to 25,000 nm. Therefore, IR excites different vibrational modes of molecular bonds. These vibrational modes are typically quantized, producing resonant or absorbance peaks, which can be mapped to specific compounds. Subtle differences in peak distributions can lead to what is commonly known as the chemical fingerprint of a sample (e.g., in the infrared region). Since their inception, these techniques have evolved from using scanning spectrometers to using Fourier-Transform Infrared Spectroscopy up to dual/triple/quadruple/n-comb spectroscopy. Additionally, diverse probing techniques have been employed to deliver the infrared light to the sample. The most common probing techniques include transmission, absorption, diffuse reflection, and attenuated total reflection. Recent technological advances can allow the monitoring of reactions by using peak identification and tracking, e.g., as the compounds evolve from initial components to end products. Real-time, or pseudo-real-time, spectrum results can be de-convoluted, compared to previously known spectra, and based on interpolations and other algorithms from which evolution of the reaction can be calculated.

Oil aging of rocks is a process in which the wettability of the surface of the rocks is changed from water-wet to oil-wet. The aim of such processes is to recreate the original state of the rocks in reservoir conditions. The processes can involve several steps in which the rock surface is conditioned with brine and submerged in oil in conditions that, as close as possible, mimic actual reservoir conditions. Although these are mainly empirical processes, some techniques are commonly used to speed up the aging process, such as (ultra) centrifugation and differential pressures (e.g., including vacuum/high pressure). There are multiple hypotheses as to why the aging process alters the wettability. Nevertheless, wettability is often attributed to complex dynamic mechanisms that are relatively poorly understood at the molecular level. Physiochemical properties of samples, such as porosity, weight, open pore volume, and others, can be measured throughout the process in order to establish baselines and track changes. Obtaining these types of measurements can often be difficult and time-consuming.

SUMMARY

The present disclosure describes techniques for using photonic techniques to conduct contactless measurements of rock wettability. In some implementations, a computer-implemented method includes the following. Rock and oil electromagnetic baselines are determined for rock samples in at least a section of an electromagnetic spectrum ranging from ultraviolet to long terahertz radiation. An aging process is conducted on each rock sample, initially starting with the rock and oil electromagnetic baselines. The aging process is repeated using spectrometry on the rock sample and measured wettabilities of the rock sample until changes in spectra are less than a predetermined threshold. Aging information including the spectra and wettabilities are stored in a machine learning database. Spectra are obtained from an unknown rock sample. The spectra are mapped to clusters in the machine learning database. Wettability ranges are determined for the unknown rock sample based on a mapping of the spectra of the unknown rock sample to clusters in the machine learning database.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method, the instructions stored on the non-transitory, computer-readable medium.

The subject matter described in this specification can be implemented in particular implementations, so as to realize one or more of the following advantages. Current solutions typically center on using chemicals to assess the wettability change of the rock and oil surface. Techniques of the present disclosure initially utilize samples of rocks and crude oil only to evaluate the sole "fingerprint" of wettability during an aging progression of the sample. This makes it possible to extrapolate further to the wettability identification of other rock samples without further treatment. Techniques of the present disclosure can be integrated directly into special core analysis processes since the techniques are non-destructive and non-altering. Moreover, the techniques can be implemented with little delay in processes in which comb spectroscopy is used. The techniques of the present disclosure provide an improvement over current wettability assessment of rocks that requires sample manipulation, preparation, and insertion into dedicated measuring equipment/environments. The techniques of the present disclosure can produce a simple and contactless process for rapid rock wettability assessment and inference. Moreover, the techniques of the present disclosure provide the potential to be adaptable into in-operando or in-situ wettability, characterization of ageing process, contamination, and liquid imbibition direct or indirect assessment techniques.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

Like reference numbers and designations in the various drawings indicate like elements.

DETAILED DESCRIPTION

Figure 1:
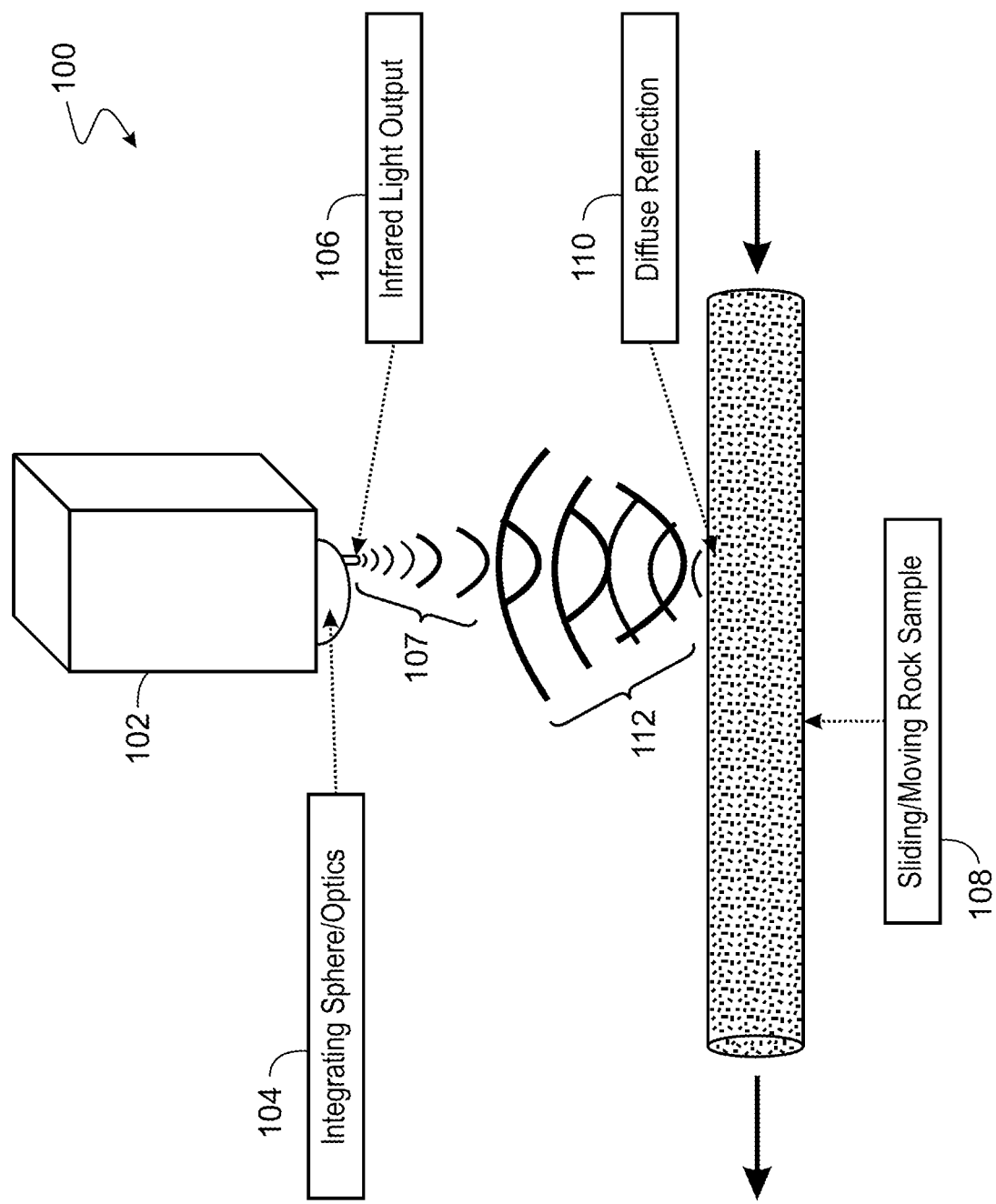
FIG. 1 is a diagram showing an example system for providing a diffuse reflectance infrared spectrometer for rock characterization.

The following detailed description describes techniques for using photonic techniques to conduct contactless measurements of rock wettability. The techniques can be extended to the geochemical analysis of rocks and fluids. The techniques are related to advanced sensing and core and rock wettability assessment. Successful proof of concept for the techniques was produced in a lab. Various modifications, alterations, and permutations of the disclosed implementations can be made and will be readily apparent to those of ordinary skill in the art, and the general principles defined may be applied to other implementations and applications, without departing from the scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

Techniques of the present disclosure include the use of infrared spectroscopy to measure the wettability change of rocks. Electromagnetic spectroscopy can provide chemical fingerprints of compounds since segments of the spectrum, e.g. infrared spectroscopy, can probe directly into molecular bonds of compounds in samples. Although no chemical reactions occur between the oil and the rock during the oil aging process, a set of markers can be identified that change along the process. These markers can be correlated to the wettability state of the rock sample. These types of measurement methodologies have applications for initial core wettability assessment without any further preparation as well as for monitoring aging processes.

A contactless method can be used to identify the wettability state of diverse types of rocks during the aging process. During development, testing, and experimentation, spectra were collected at different spots of the rock surface by diffuse reflected Fourier-transform infrared spectroscopy (FTIR), also known as Diffuse Reflection Infrared Fourier Transform Spectroscopy (DRIFT). The spectra were collected before, during, and after the aging process. These initial and other measurements provide a baseline of the rock sample's fingerprint. In addition, an oil sample can also be characterized as part of the baseline. During testing and experimentation, DRIFT surface measurements were taken during the aging process, capturing the chemical transformation of the rock's surface during the aging process. This information was supplemented by other wettability measurements (such as contact angle) in order to correlate to other commonly-known engineering parameters. Common processing of spectra includes the subtraction of the rock and oil baseline or the initial submerged rock in an oil baseline.

Techniques of the present disclosure are not limited to DRIFT spectrometry. The techniques can employ, or be extended to, diffuse reflection (e.g., dual/triple/n-tuple) comb spectroscopy, attenuated total reflectance (ATR) FTIR, ATR (dual/triple/n-tuple) comb spectroscopy, and transmission FTIR/DSC (differential scanning calorimetry) using thin sections of rocks.

During development, testing, and experimentation, the samples were mapped into clusters (database) using K-MEANS and t-SNE to identify the wettability labels. Other techniques can include principal component analysis (PCA), KSense, or label free machine learning. Thereafter, techniques for wettability inference can be used such as singular value decomposition (SVD), random-forest, XGBoost, CatBoost, deep/convolutional neural network, or other machine learning methods. These techniques can also be employed to infer other properties, e.g., rock and/or oil type. With the help of these mathematical and computational tools, the visualization and/or identification processes for samples can become simpler. Additionally, spectral acquisition and computational wettability inference can be performed in seconds or fractions of a second, e.g., using the latest frequency comb technologies for electromagnetic (EM) spectroscopy e.g. ultraviolet (UV), infrared (IR) and Terahertz spectroscopy. In addition, the use of computational and/or machine learning algorithms need not be limited to evaluating peaks, but can also be used to evaluate subtler tendencies and elements within the spectra that are not obvious to the naked eye or by using traditional peak identification algorithms. Moreover, the estimation of wettability can become more accurate by increasing the number of samples in a cluster/database. This technique could be complemented and/or integrated with other photonic/optical methods such as optical (visible light) cameras, nuclear magnetic resonance (NMR), and microwave spectroscopy. As such, the techniques need not be limited to laboratory rock wettability techniques. For example, the techniques can be used as in-operando characterization techniques for special core analysis during extraction with the potential to become a routine core analysis tool, as well as for rock wettability assessment during drilling operations.

FIG. 1 is a diagram showing an example system 100 for providing a diffuse reflectance infrared spectrometer for rock characterization. This setup of the system 100 is indistinct of the spectrometry method employed; e.g. scanning IR, FTIR, DSC, and thermo-stimulated current (TSC). The system 100 includes a controller 102 that includes integrating sphere and in/out-coupling optics 104 and an electromagnetic (EM) radiation source, e.g., in between UV and far terahertz light, output 106 outputting a signal 107. The signal 107 hits a static or sliding/moving rock sample 108, resulting in a diffuse reflection, refraction or scattering 110 and a reflected signal 112. Further embodiments can entail the use of rock, cuttings, or simply samples sliding over a conveyor belt or rods system; in-line cleaning systems such as sprays, fans, blowers, and/or tanks with a plurality of solvents, surfactants and/or brines; the use of the source/sensor (102) mounted on a robotic arm, Cartesian frame or used with a spatiotemporal light modulator mounted to an angle, e.g., perpendicular, to the average surface of the sample.

Figure 2:
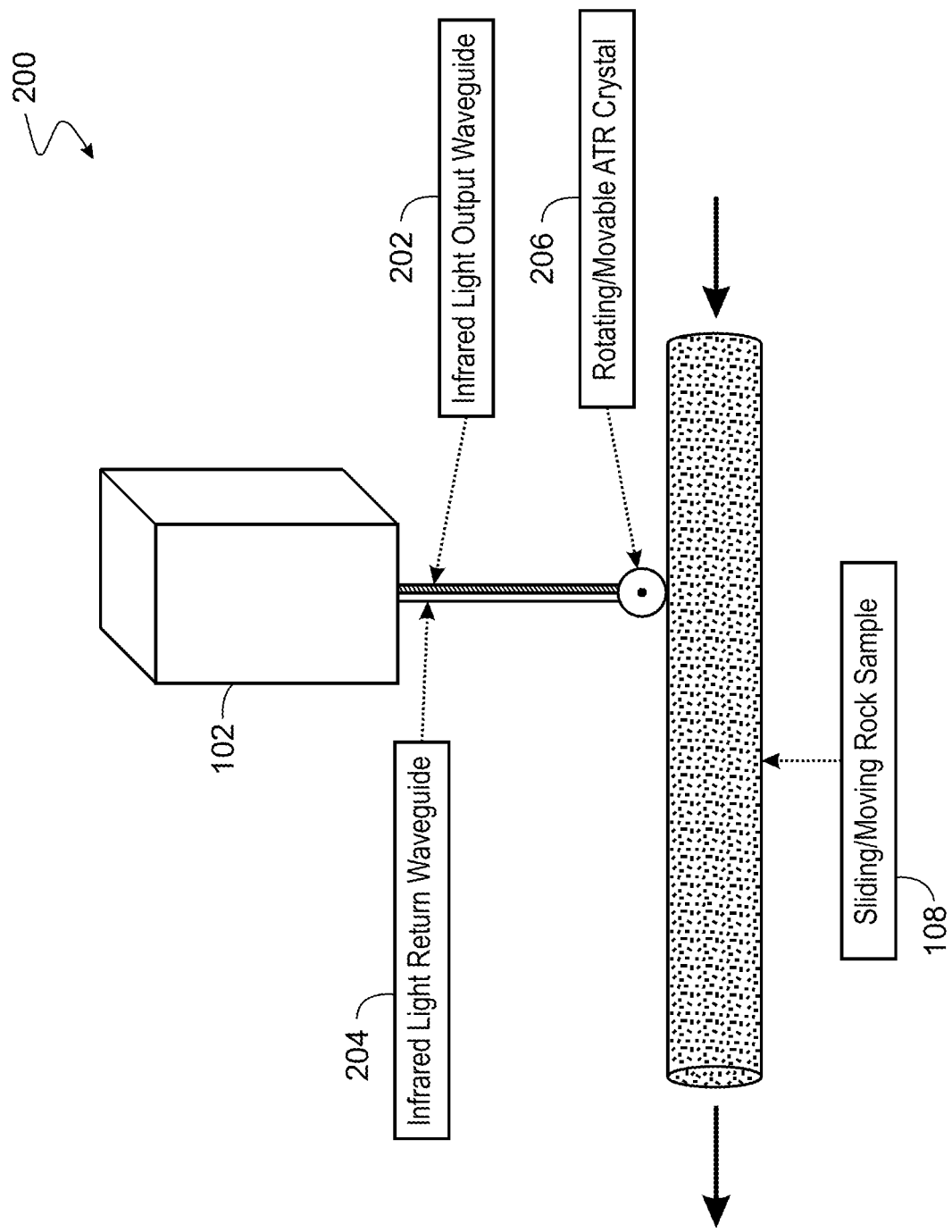
FIG. 2 is a diagram showing an example system for providing an attenuated total reflectance (ATR) infrared spectrometer, according to some implementations of the present disclosure.

FIG. 2 is a diagram showing an example system 200 for providing an ATR infrared spectrometer, according to some implementations of the present disclosure. This setup of the system 200 is indistinct of the spectrometry method employed (e.g., scanning IR, FTIR, DSC, transmission crystal spectrometry (TCS), etc.). The system 200 includes a controller 102 that includes an UV to far terahertz output waveguide 202, an UV to far terahertz light return wavelength 204, and a rotating/movable ATR crystal 206, comprised of a material such as diamond, silicon, zinc selenide, and/or germanium with an optional coating with self-cleaning capabilities, e.g., mild to super: hydrophobicity, oleophobicity, and/or omniphobicity, or meta-surfaces for signal to noise ratio.

Figure 3:
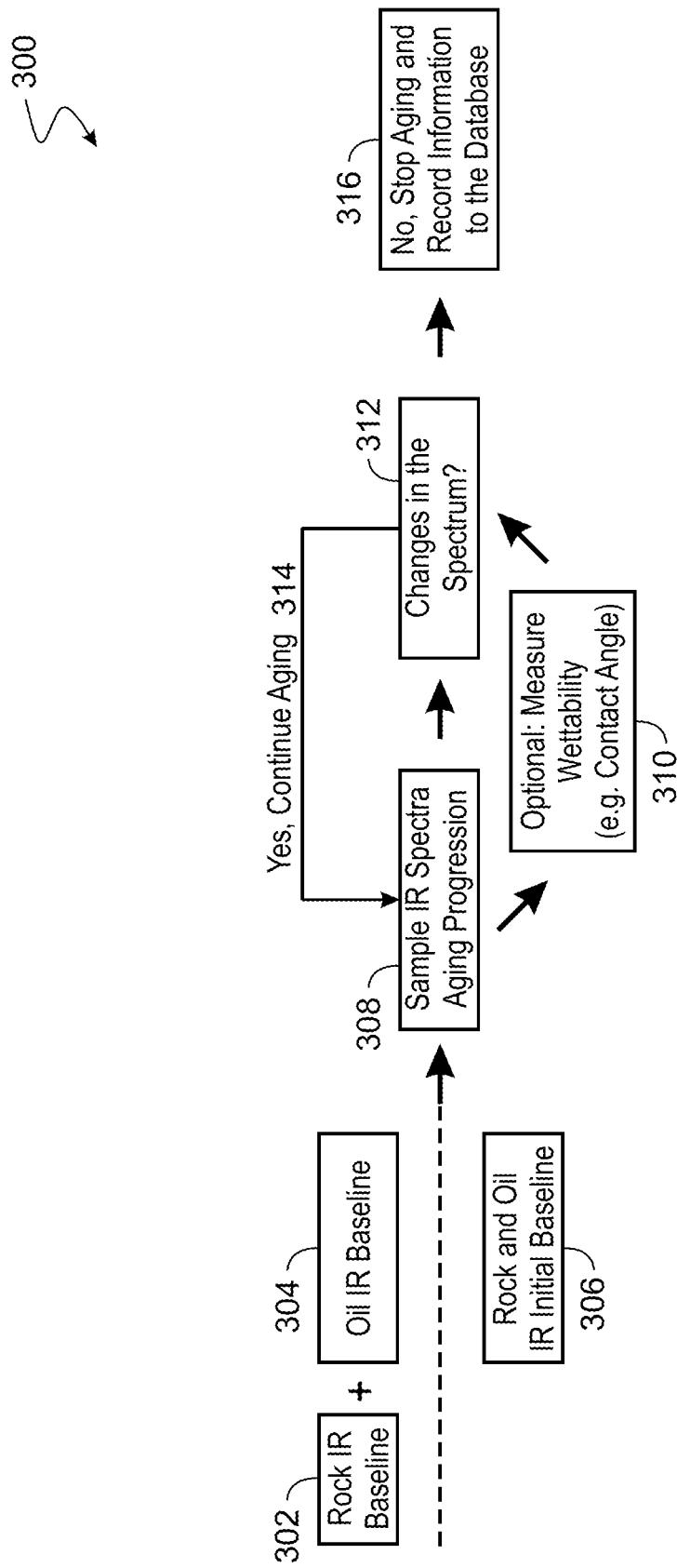
FIG. 3 is a flow diagram showing an example of a workflow for initial measurements and database creation for the correlation of infrared spectrum to rock wettability, according to some implementations of the present disclosure

FIG. 3 is a flow diagram showing an example of a workflow 300 for initial measurements and database creation for the correlation of infrared spectrum to rock wettability, according to some implementations of the present disclosure. The workflow 300 uses a rock IR database 302 and an oil IR baseline 304 (or a combined rock and oil EM initial baseline 306). At 308, sample IR spectra aging begins. At 312, wettability is optionally measured (e.g., using the contact angle). At 310, a determination is made whether changes in the spectrum 310 are still occurring. For example, the algorithm can process the EM spectra and determine whether changes have occurred (e.g., above a threshold of a 10% or less change depending on application) and track the wettability state continuously until some given value is attained. At 314, if changes are still occurring, then aging continues. Otherwise, at 316, aging is stopped and information is recorded to the database 316. Once the machine learning (ML) database is available, then it is possible to automate the aging process. In this case, the optional step (wettability optionally measured using contact angle) can be avoided since the wettability state can be derived from the EM spectra using the ML. Multiple ML algorithms can be employed. Initially XGBoost and forest tree methods can provide a quick wettability classifier. Generative adversarial networks (GANs), such as U-Net, can be used to find qualitative mappings (regression) between the spectral signature and the wettability values.

Figure 4:
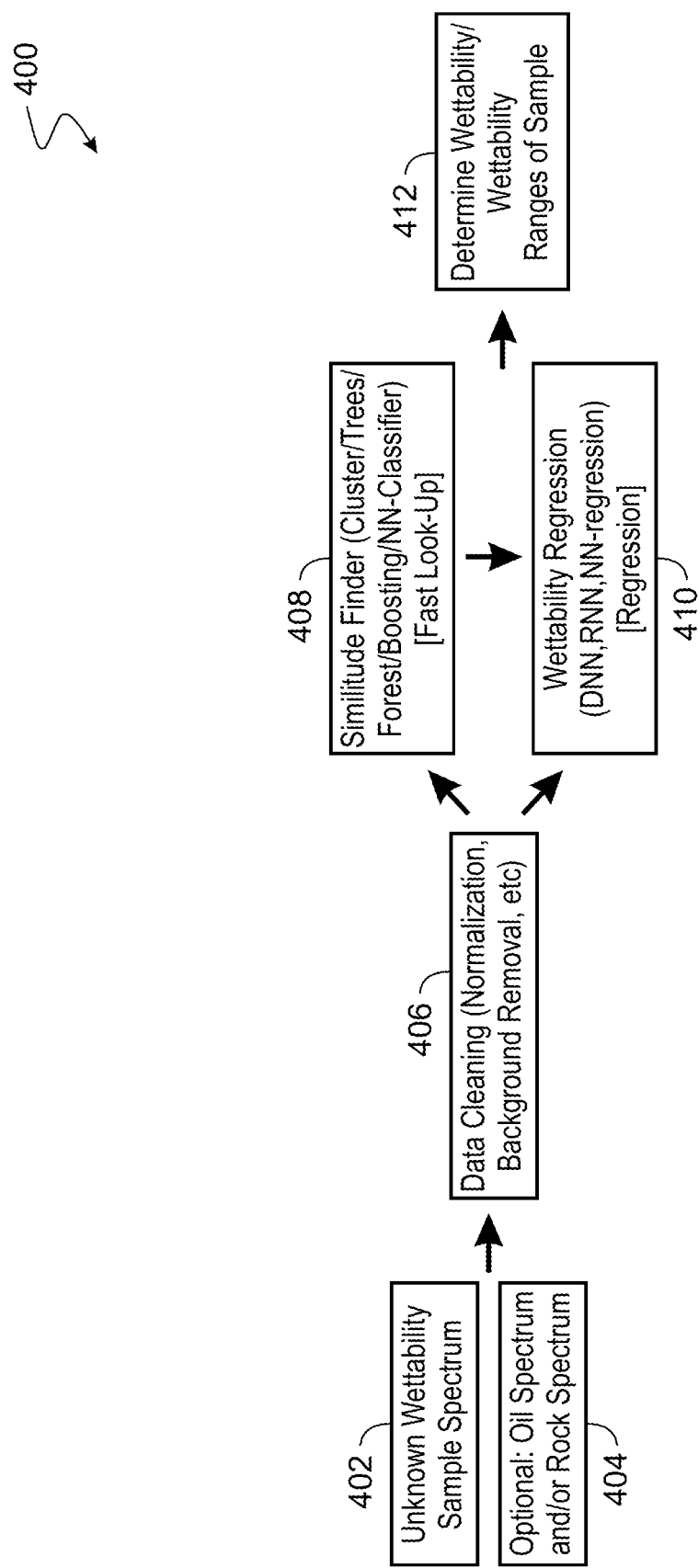
FIG. 4 is a flow diagram showing an example of a workflow for an assessment of the wettability of unknown rock samples, according to some implementations of the present disclosure.

FIG. 4 is a flow diagram showing an example of a workflow 400 for an assessment of the wettability of unknown rock samples, according to some implementations of the present disclosure. At 402, the wettability of an unknown sample is obtained. At 404, an oil spectrum and/or a rock spectrum is optionally obtained. At 406, data cleaning occurs, including normalization and background removal. At 408, a similitude finder is executed, including clustering, tree/forest boosting, and NN classification (e.g., using a fast look-up). At 410, wettability regression is performed (e.g., using deep neural network (DNN), recurrent neural network (RNN), or neural network (NN)-regression). At 412, wettability is determined, e.g., as a wettability range.

In the workflow 400, the baseline and post-process spectra are cleaned and passed to either 1) a similitude finder (also known as a fast look-up or clustering) to determine if the spectra belong to some set of known wettability values (e.g., using clustering or classification) or an outlier (e.g., using anomaly detection); or 2) a regression algorithm that uses the spectra to derive the wettability value. Note that in some embodiments it can be possible to go straight from the spectra to regression. Furthermore, the regression step can be simplified to a classification process by providing a set of wettability ranges arranged in groups.

Figure 5:
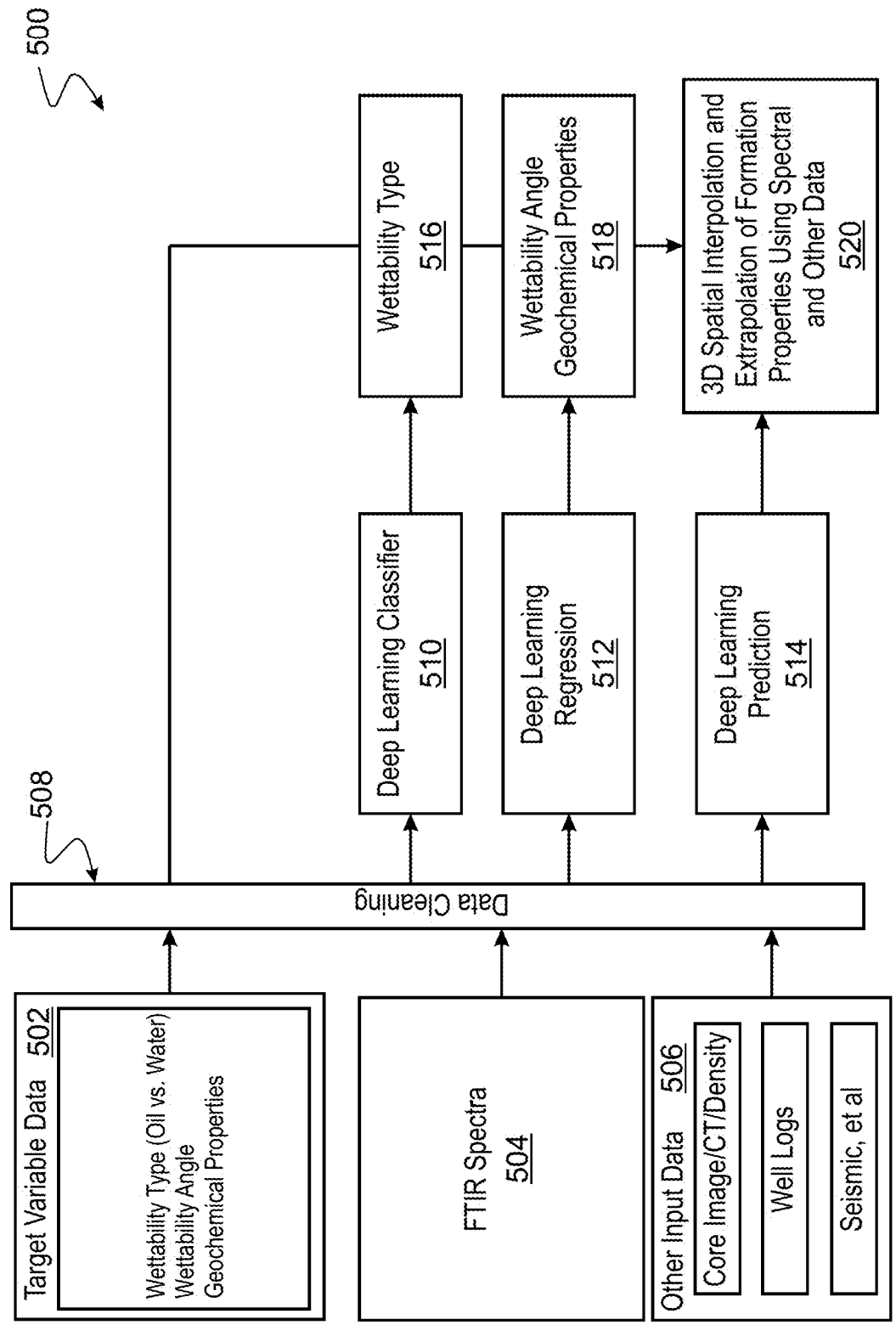
FIG. 5 is a flow diagram showing an example of a workflow for generating a machine learning model for wettability classification and regression, according to some implementations of the present disclosure.

FIG. 5 is a flow diagram showing an example of a workflow 500 for generating a machine learning model for wettability classification and regression, according to some implementations of the present disclosure. The workflow 500 uses target variable data 502 (including wettability type, oil versus water, wettability angle, and geochemical properties), FTIR spectra 504, and other input data 506 (e.g., including core image, computerized tomography (CT), density data, well logs, and seismic data). At 508, data cleaning occurs. Using the clean data, the workflow 500 includes execution of a deep learning classifier 510, deep learning regression 512, and deep learning prediction 514. Outputs of the workflow 500 include a wettability type 516, a wettability angle and geochemical properties 518, biological properties, and three-dimensional (3D) spatial interpretation and extrapolation of formation properties using spectral and other data 520.

The model can be expanded to the characterization of other geochemical properties, given that the EM spectra, e.g., IR, already provides information about mineral and fluid properties. The deep learning models can be tasked with subtracting and de-convolving the spectral image(s) for that purpose. The initial feed to the workflow 500 can be composed of concatenated tensors (parallel or serial concatenation of the spectra). Let M be the number of measurements taken, e.g., baselines plus any number of real-time spectra. The term real-time can correspond, for example, to events that occur within a specified period of time, such as within one minute. Let N be the number of frequencies recorded. Parallel concatenation yields a two-dimensional (2D) tensor with the following dimensions: M-measurements×N-frequencies with the intensity values assigned to every (M, N) pair. A serial concatenation yields a (M×N) 1D tensor of intensity values. The intensity of the spectra can be normalized to some given value, e.g., frequency-by-frequency according to irradiance of the source, or the maximum peak from the experiment run. It is also possible to build a 3D tensor with M-measurements×P-discretized intensities×N-frequencies.

Figure 6:
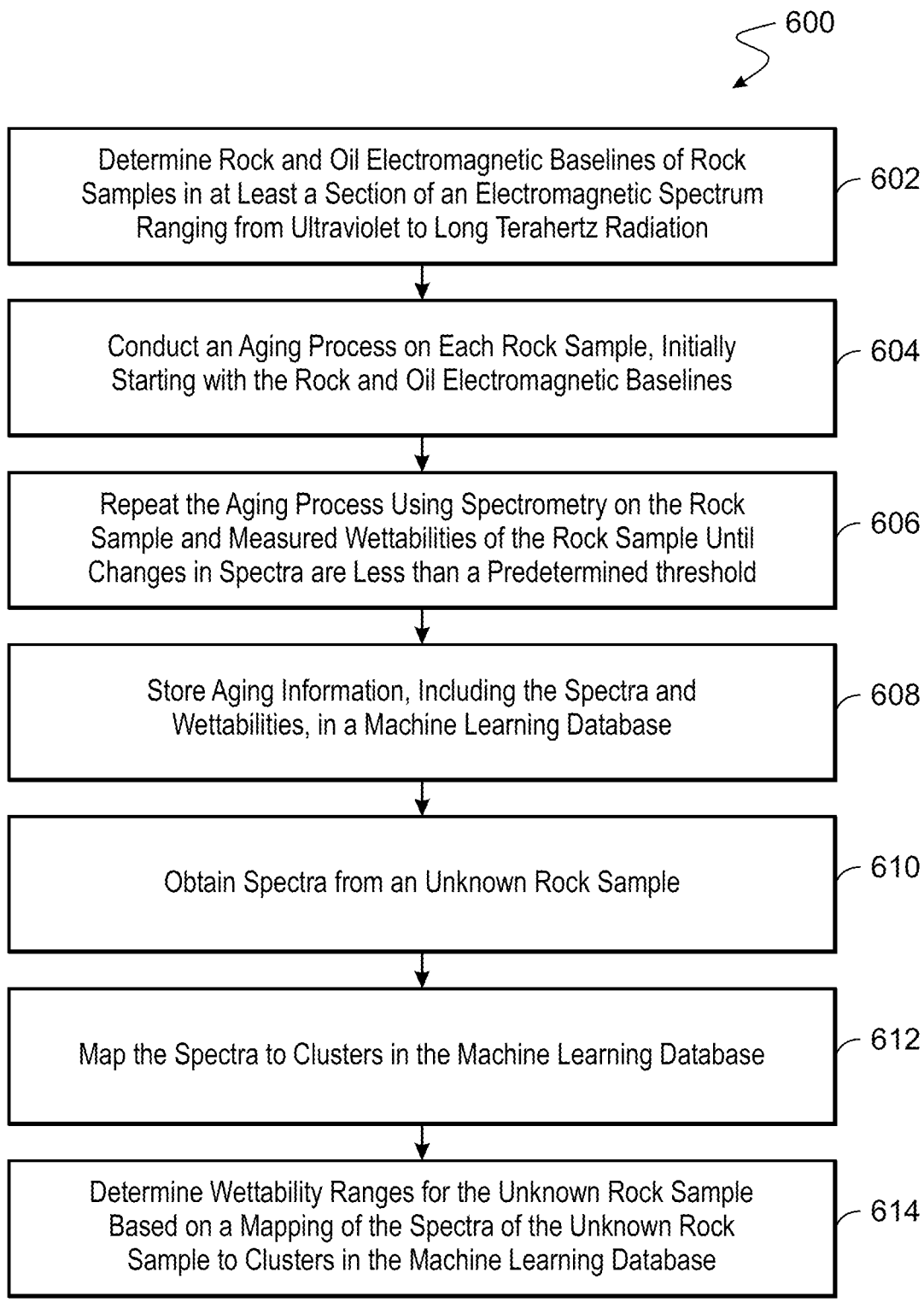
FIG. 6 is a flowchart of an example of a method for determining wettability ranges for an unknown rock sample, according to some implementations of the present disclosure

FIG. 6 is a flowchart of an example of a method 600 for determining wettability ranges for an unknown rock sample, according to some implementations of the present disclosure. For clarity of presentation, the description that follows generally describes method 600 in the context of the other figures in this description. However, it will be understood that method 600 can be performed, for example, by any suitable system, environment, software, and hardware, or a combination of systems, environments, software, and hardware, as appropriate. In some implementations, various steps of method 600 can be run in parallel, in combination, in loops, or in any order. In some implementations, method 600 can use computational databases.

At 602, rock and oil infrared baselines of rock samples are determined. The baselines can be determined using the workflow 300, for example. From 602, method 600 proceeds to 604.

At 604, an aging process, initially starting with the rock and oil infrared baselines, is conducted on each rock sample. The aging process can be conducted using the workflow 300, for example. From 604, method 600 proceeds to 606.

At 606, the aging process is repeated using spectrometry on the rock sample and measured wettabilities of the rock sample until changes in spectra are less than a predetermined threshold. For example, the predetermined threshold can be a 10% change or below. From 606, method 600 proceeds to 608.

At 608, aging information including the spectra and wettabilities are stored in a machine learning database. From 608, method 600 proceeds to 610.

At 610, spectra are obtained from an unknown rock sample. For example, unknown rock sample can be the sliding/moving rock sample 108. For example, obtaining the spectra from the unknown rock sample 108 can include using integrating sphere/optics 104 providing an infrared light output 106, as described with reference to FIG. 1. Obtaining the spectra from the unknown rock sample can include processing a diffuse reflection 110 from the unknown rock sample 108. In some implementations, obtaining the spectra from the unknown rock sample can include: sending a light output to the unknown rock sample 108 using an infrared light output waveguide 202; and receiving light from the unknown rock sample 108 using an infrared light return waveguide 204, as described with reference to FIG. 2. A rotating/movable ATR crystal 206 can be used. From 610, method 600 proceeds to 612.

At 612, the spectra are mapped to clusters in the machine learning database. The mapping can occur as described with reference to FIG. 4, for example. From 612, method 600 proceeds to 614.

At 614, wettability ranges are determined for the unknown rock sample based on a mapping of the spectra of the unknown rock sample to clusters in the machine learning database. After 614, method 600 can stop.

In some implementations, in addition to (or in combination with) any previously-described features, techniques of the present disclosure can include the following. Outputs of the techniques of the present disclosure can be performed before, during, or in combination with wellbore operations, such as to provide inputs to change the settings or parameters of equipment used for drilling, exploration, and stimulation. Examples of wellbore operations include forming/drilling a wellbore, hydraulic fracturing, and producing through the wellbore, to name a few. Examples of exploration include characterization subsurface or surface solids, fluids, or a combination of both with the intent of identifying prospects for energy extraction and storage. Examples of stimulation include operations where the characterization of fluids of rocks can be use as guide to determine payload zones, characterizing the effects of stimulation methods, and determine fluid quality. The wellbore operations can be triggered or controlled, for example, by outputs of the methods of the present disclosure. In some implementations, customized user interfaces can present intermediate or final results of the above described processes to a user. Information can be presented in one or more textual, tabular, or graphical formats, such as through a dashboard. The information can be presented at one or more on-site locations (such as at an oil well or other facility), on the Internet (such as on a webpage), on a mobile application (or "app"), or at a central processing facility. The presented information can include suggestions, such as suggested changes in parameters or processing inputs, that the user can select to implement improvements in a production environment, such as in the exploration, production, and/or testing of petrochemical processes or facilities. For example, the suggestions can include parameters that, when selected by the user, can cause a change to, or an improvement in, drilling parameters (including drill bit speed and direction) or overall production of a gas or oil well. The suggestions, when implemented by the user, can improve the speed and accuracy of calculations, streamline processes, improve models, and solve problems related to efficiency, performance, safety, reliability, costs, downtime, and the need for human interaction. In some implementations, the suggestions can be implemented in real-time, such as to provide an immediate or near-immediate change in operations or in a model. The term real-time can correspond, for example, to events that occur within a specified period of time, such as within one minute or within one second. Events can include readings or measurements captured by downhole equipment such as sensors, pumps, bottom hole assemblies, or other equipment. The readings or measurements can be analyzed at the surface, such as by using applications that can include modeling applications and machine learning. The analysis can be used to generate changes to the settings of downhole equipment, such as drilling equipment. In some implementations, values of parameters or other variables that are determined can be used automatically (such as through using rules) to implement changes in oil or gas well exploration, production/drilling, or testing. For example, outputs of the present disclosure can be used as inputs to other equipment and/or systems at a facility. This can be especially useful for systems or various pieces of equipment that are located several meters or several miles apart, or are located in different countries or other jurisdictions.

Figure 7:
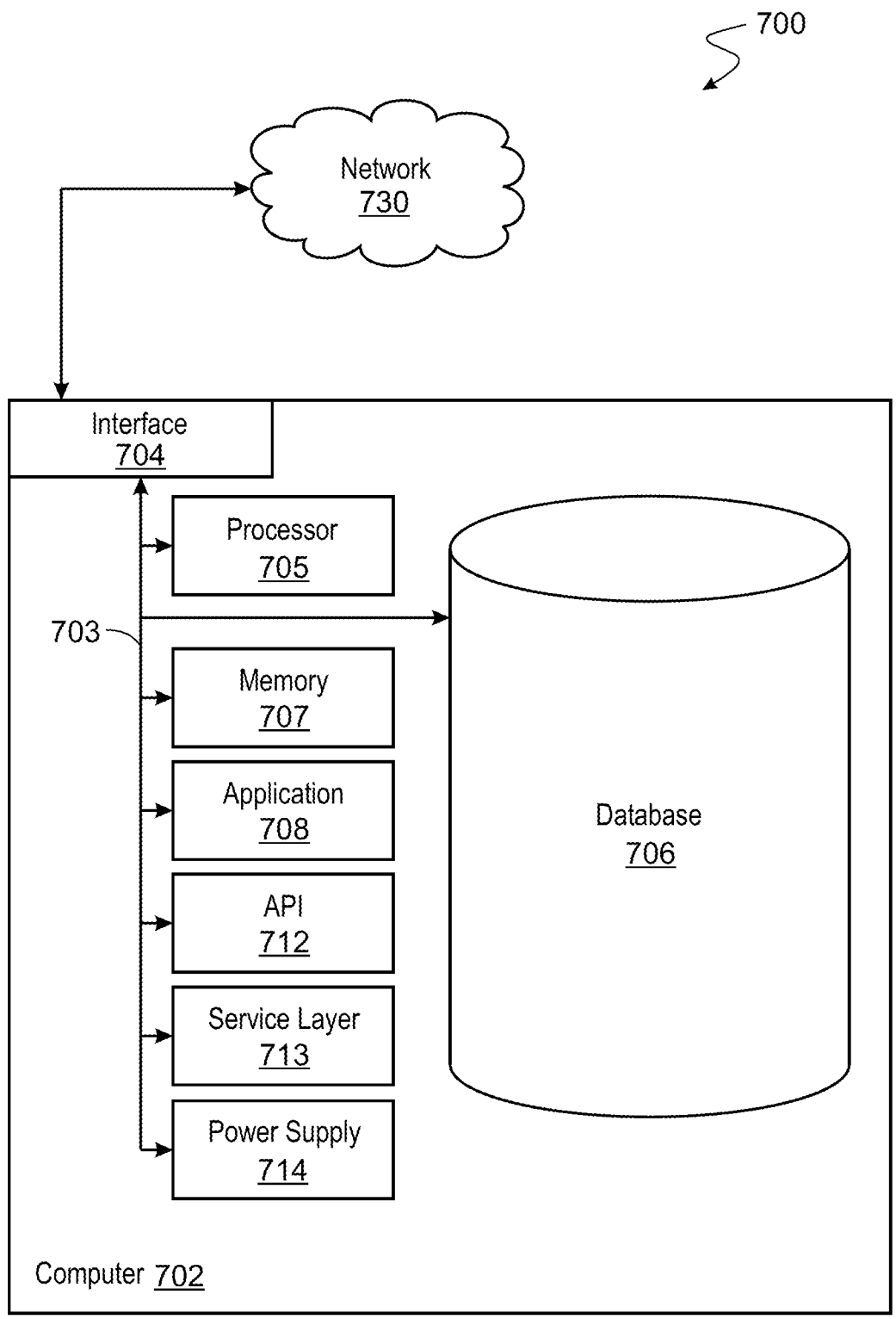
FIG. 7 is a block diagram illustrating an example computer system used to provide computational functionalities associated with described algorithms, methods, functions, processes, flows, and procedures as described in the present disclosure, according to some implementations of the present disclosure.

FIG. 7 is a block diagram of an example computer system 700 used to provide computational functionalities associated with described algorithms, methods, functions, processes, flows, and procedures described in the present disclosure, according to some implementations of the present disclosure. The illustrated computer 702 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 702 can include input devices such as keypads, keyboards, and touch screens that can accept user information. Also, the computer 702 can include output devices that can convey information associated with the operation of the computer 702. The information can include digital data, visual data, audio information, or a combination of information. The information can be presented in a graphical user interface (UI) (or GUI).

The computer 702 can serve in a role as a client, a network component, a server, a database, a persistency, or components of a computer system for performing the subject matter described in the present disclosure. The illustrated computer 702 is communicably coupled with a network 730. In some implementations, one or more components of the computer 702 can be configured to operate within different environments, including cloud-computing-based environments, local environments, global environments, and combinations of environments.

At a top level, the computer 702 is an electronic computing device operable to receive, transmit, process, store, and manage data and information associated with the described subject matter. According to some implementations, the computer 702 can also include, or be communicably coupled with, an application server, an email server, a web server, a caching server, a streaming data server, or a combination of servers.

The computer 702 can receive requests over network 730 from a client application (for example, executing on another computer 702). The computer 702 can respond to the received requests by processing the received requests using software applications. Requests can also be sent to the computer 702 from internal users (for example, from a command console), external (or third) parties, automated applications, entities, individuals, systems, and computers.

Each of the components of the computer 702 can communicate using a system bus 703. In some implementations, any or all of the components of the computer 702, including hardware or software components, can interface with each other or the interface 704 (or a combination of both) over the system bus 703. Interfaces can use an application programming interface (API) 712, a service layer 713, or a combination of the API 712 and service layer 713. The API 712 can include specifications for routines, data structures, and object classes. The API 712 can be either computer-language independent or dependent. The API 712 can refer to a complete interface, a single function, or a set of APIs.

The service layer 713 can provide software services to the computer 702 and other components (whether illustrated or not) that are communicably coupled to the computer 702. The functionality of the computer 702 can be accessible for all service consumers using this service layer. Software services, such as those provided by the service layer 713, can provide reusable, defined functionalities through a defined interface. For example, the interface can be software written in JAVA, C++, or a language providing data in extensible markup language (XML) format. While illustrated as an integrated component of the computer 702, in alternative implementations, the API 712 or the service layer 713 can be stand-alone components in relation to other components of the computer 702 and other components communicably coupled to the computer 702. Moreover, any or all parts of the API 712 or the service layer 713 can be implemented as child or sub-modules of another software module, enterprise application, or hardware module without departing from the scope of the present disclosure.

The computer 702 includes an interface 704. Although illustrated as a single interface 704 in FIG. 7, two or more interfaces 704 can be used according to particular needs, desires, or particular implementations of the computer 702 and the described functionality. The interface 704 can be used by the computer 702 for communicating with other systems that are connected to the network 730 (whether illustrated or not) in a distributed environment. Generally, the interface 704 can include, or be implemented using, logic encoded in software or hardware (or a combination of software and hardware) operable to communicate with the network 730. More specifically, the interface 704 can include software supporting one or more communication protocols associated with communications. As such, the network 730 or the interface's hardware can be operable to communicate physical signals within and outside of the illustrated computer 702.

The computer 702 includes a processor 705. Although illustrated as a single processor 705 in FIG. 7, two or more processors 705 can be used according to particular needs, desires, or particular implementations of the computer 702 and the described functionality. Generally, the processor 705 can execute instructions and can manipulate data to perform the operations of the computer 702, including operations using algorithms, methods, functions, processes, flows, and procedures as described in the present disclosure.

The computer 702 also includes a database 706 that can hold data for the computer 702 and other components connected to the network 730 (whether illustrated or not). For example, database 706 can be an in-memory, conventional, or a database storing data consistent with the present disclosure. In some implementations, database 706 can be a combination of two or more different database types (for example, hybrid in-memory and conventional databases) according to particular needs, desires, or particular implementations of the computer 702 and the described functionality. Although illustrated as a single database 706 in FIG. 7, two or more databases (of the same, different, or combination of types) can be used according to particular needs, desires, or particular implementations of the computer 702 and the described functionality. While database 706 is illustrated as an internal component of the computer 702, in alternative implementations, database 706 can be external to the computer 702.

The computer 702 also includes a memory 707 that can hold data for the computer 702 or a combination of components connected to the network 730 (whether illustrated or not). Memory 707 can store any data consistent with the present disclosure. In some implementations, memory 707 can be a combination of two or more different types of memory (for example, a combination of semiconductor and magnetic storage) according to particular needs, desires, or particular implementations of the computer 702 and the described functionality. Although illustrated as a single memory 707 in FIG. 7, two or more memories 707 (of the same, different, or combination of types) can be used according to particular needs, desires, or particular implementations of the computer 702 and the described functionality. While memory 707 is illustrated as an internal component of the computer 702, in alternative implementations, memory 707 can be external to the computer 702.

The application 708 can be an algorithmic software engine providing functionality according to particular needs, desires, or particular implementations of the computer 702 and the described functionality. For example, application 708 can serve as one or more components, modules, or applications. Further, although illustrated as a single application 708, the application 708 can be implemented as multiple applications 708 on the computer 702. In addition, although illustrated as internal to the computer 702, in alternative implementations, the application 708 can be external to the computer 702.

The computer 702 can also include a power supply 714. The power supply 714 can include a rechargeable or non-rechargeable battery that can be configured to be either user- or non-user-replaceable. In some implementations, the power supply 714 can include power-conversion and management circuits, including recharging, standby, and power management functionalities. In some implementations, the power supply 714 can include a power plug to allow the computer 702 to be plugged into a wall socket or a power source to, for example, power the computer 702 or recharge a rechargeable battery.

There can be any number of computers 702 associated with, or external to, a computer system containing computer 702, with each computer 702 communicating over network 730. Further, the terms "client," "user," and other appropriate terminology can be used interchangeably, as appropriate, without departing from the scope of the present disclosure. Moreover, the present disclosure contemplates that many users can use one computer 702 and one user can use multiple computers 702.

Described implementations of the subject matter can include one or more features, alone or in combination.

For example, in a first implementation, a computer-implemented method includes the following. Rock and oil electromagnetic baselines are determined for rock samples in at least a section of an electromagnetic spectrum ranging from ultraviolet to long terahertz radiation. An aging process is conducted on each rock sample, initially starting with the rock and oil electromagnetic baselines. The aging process is repeated using spectrometry on the rock sample and measured wettabilities of the rock sample until changes in spectra are less than a predetermined threshold. Aging information including the spectra and wettabilities are stored in a machine learning database. Spectra are obtained from an unknown rock sample. The spectra are mapped to clusters in the machine learning database. Wettability ranges are determined for the unknown rock sample based on a mapping of the spectra of the unknown rock sample to clusters in the machine learning database.

The foregoing and other described implementations can each, optionally, include one or more of the following features:

A first feature, combinable with any of the following features, where the unknown rock sample is a sliding/moving rock sample.

A second feature, combinable with any of the previous or following features, where obtaining the spectra from the unknown rock sample includes integrating sphere/optics providing an light output in at least a section of the electromagnetic spectrum ranging from the ultraviolet to the long terahertz radiation.

A third feature, combinable with any of the previous or following features, where obtaining the spectra from the unknown rock sample includes processing a diffuse reflection from the unknown rock sample.

A fourth feature, combinable with any of the previous or following features, where obtaining the spectra from the unknown rock sample includes: sending a light output to the unknown rock sample using a light output waveguide in at least a section of the electromagnetic spectrum ranging from the ultraviolet to the long terahertz radiation; and receiving light from the unknown rock sample using a light return waveguide in at least a section of the electromagnetic spectrum ranging from the ultraviolet to the long terahertz radiation.

A fifth feature, combinable with any of the previous or following features, where the method further includes using a rotating/movable attenuated total reflectance (ATR) crystal.

A sixth feature, combinable with any of the previous or following features, where the predetermined threshold is a 10% change or less.

In a second implementation, a non-transitory, computer-readable medium stores one or more instructions executable by a computer system to perform operations including the following. Rock and oil electromagnetic baselines are determined for rock samples in at least a section of an electromagnetic spectrum ranging from ultraviolet to long terahertz radiation. An aging process is conducted on each rock sample, initially starting with the rock and oil electromagnetic baselines. The aging process is repeated using spectrometry on the rock sample and measured wettabilities of the rock sample until changes in spectra are less than a predetermined threshold. Aging information including the spectra and wettabilities are stored in a machine learning database. Spectra are obtained from an unknown rock sample. The spectra are mapped to clusters in the machine learning database. Wettability ranges are determined for the unknown rock sample based on a mapping of the spectra of the unknown rock sample to clusters in the machine learning database.

The foregoing and other described implementations can each, optionally, include one or more of the following features:

A first feature, combinable with any of the following features, where the unknown rock sample is a sliding/moving rock sample.

A second feature, combinable with any of the previous or following features, where obtaining the spectra from the unknown rock sample includes integrating sphere/optics providing an light output in at least a section of the electromagnetic spectrum ranging from the ultraviolet to the long terahertz radiation.

A third feature, combinable with any of the previous or following features, where obtaining the spectra from the unknown rock sample includes processing a diffuse reflection from the unknown rock sample.

A fourth feature, combinable with any of the previous or following features, where obtaining the spectra from the unknown rock sample includes: sending a light output to the unknown rock sample using a light output waveguide in at least a section of the electromagnetic spectrum ranging from the ultraviolet to the long terahertz radiation; and receiving light from the unknown rock sample using a light return waveguide in at least a section of the electromagnetic spectrum ranging from the ultraviolet to the long terahertz radiation.

A fifth feature, combinable with any of the previous or following features, where the operations further includes using a rotating/movable attenuated total reflectance (ATR) crystal.

A sixth feature, combinable with any of the previous or following features, where the predetermined threshold is a 10% change or less.

In a third implementation, a computer-implemented system includes one or more processors and a non-transitory computer-readable storage medium coupled to the one or more processors and storing programming instructions for execution by the one or more processors. The programming instructions instruct the one or more processors to perform operations including the following. Rock and oil electromagnetic baselines are determined for rock samples in at least a section of an electromagnetic spectrum ranging from ultraviolet to long terahertz radiation. An aging process is conducted on each rock sample, initially starting with the rock and oil electromagnetic baselines. The aging process is repeated using spectrometry on the rock sample and measured wettabilities of the rock sample until changes in spectra are less than a predetermined threshold. Aging information including the spectra and wettabilities are stored in a machine learning database. Spectra are obtained from an unknown rock sample. The spectra are mapped to clusters in the machine learning database. Wettability ranges are determined for the unknown rock sample based on a mapping of the spectra of the unknown rock sample to clusters in the machine learning database.

The foregoing and other described implementations can each, optionally, include one or more of the following features:

A first feature, combinable with any of the following features, where the unknown rock sample is a sliding/moving rock sample.

A second feature, combinable with any of the previous or following features, where obtaining the spectra from the unknown rock sample includes integrating sphere/optics providing an light output in at least a section of the electromagnetic spectrum ranging from the ultraviolet to the long terahertz radiation.

A third feature, combinable with any of the previous or following features, where obtaining the spectra from the unknown rock sample includes processing a diffuse reflection from the unknown rock sample.

A fourth feature, combinable with any of the previous or following features, where obtaining the spectra from the unknown rock sample includes: sending a light output to the unknown rock sample using a light output waveguide in at least a section of the electromagnetic spectrum ranging from the ultraviolet to the long terahertz radiation; and receiving light from the unknown rock sample using a light return waveguide in at least a section of the electromagnetic spectrum ranging from the ultraviolet to the long terahertz radiation.

A fifth feature, combinable with any of the previous or following features, where the operations further includes using a rotating/movable attenuated total reflectance (ATR) crystal.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network.

Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at the application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure.

Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A computer-implemented method, comprising:
   determining rock and oil electromagnetic baselines of rock samples in at least a section of an electromagnetic spectrum ranging from ultraviolet to long terahertz radiation;
   conducting an aging process on each rock sample, initially starting with the rock and oil electromagnetic baselines;
   repeating the aging process using spectrometry on the rock sample and measured wettabilities of the rock sample until changes in spectra are less than a predetermined threshold;
   storing aging information, including the spectra and wettabilities, in a machine learning database;
   obtaining spectra from an unknown rock sample;
   mapping the spectra to clusters in the machine learning database; and
   determining wettability ranges for the unknown rock sample based on a mapping of the spectra of the unknown rock sample to clusters in the machine learning database.

2. The computer-implemented method of claim 1, wherein the unknown rock sample is a sliding/moving rock sample.

3. The computer-implemented method of claim 1, wherein obtaining the spectra from the unknown rock sample includes integrating sphere/optics providing an light output in at least a section of the electromagnetic spectrum ranging from the ultraviolet to the long terahertz radiation.

4. The computer-implemented method of claim 3, wherein obtaining the spectra from the unknown rock sample includes processing a diffuse reflection from the unknown rock sample.

5. The computer-implemented method of claim 1, wherein obtaining the spectra from the unknown rock sample includes:
   sending a light output to the unknown rock sample using a light output waveguide in at least a section of the electromagnetic spectrum ranging from the ultraviolet to the long terahertz radiation; and
   receiving light from the unknown rock sample using a light return waveguide in at least a section of the electromagnetic spectrum ranging from the ultraviolet to the long terahertz radiation.

6. The computer-implemented method of claim 5, the method further comprising using a rotating/movable attenuated total reflectance (ATR) crystal.

7. The computer-implemented method of claim 1, wherein the predetermined threshold is a 10% change or less.

8. A non-transitory, computer-readable medium storing one or more instructions executable by a computer system to perform operations comprising:
   determining rock and oil electromagnetic baselines of rock samples in at least a section of an electromagnetic spectrum ranging from ultraviolet to long terahertz radiation;
   conducting an aging process on each rock sample, initially starting with the rock and oil electromagnetic baselines;
   repeating the aging process using spectrometry on the rock sample and measured wettabilities of the rock sample until changes in spectra are less than a predetermined threshold;
   storing aging information, including the spectra and wettabilities, in a machine learning database;
   obtaining spectra from an unknown rock sample;
   mapping the spectra to clusters in the machine learning database; and
   determining wettability ranges for the unknown rock sample based on a mapping of the spectra of the unknown rock sample to clusters in the machine learning database.

9. The non-transitory, computer-readable medium of claim 8, wherein the unknown rock sample is a sliding/moving rock sample.

10. The non-transitory, computer-readable medium of claim 8, wherein obtaining the spectra from the unknown rock sample includes integrating sphere/optics providing an light output in at least a section of the electromagnetic spectrum ranging from the ultraviolet to the long terahertz radiation.

11. The non-transitory, computer-readable medium of claim 10, wherein obtaining the spectra from the unknown rock sample includes processing a diffuse reflection from the unknown rock sample.

12. The non-transitory, computer-readable medium of claim 8, wherein obtaining the spectra from the unknown rock sample includes:
   sending a light output to the unknown rock sample using a light output waveguide in at least a section of the electromagnetic spectrum ranging from the ultraviolet to the long terahertz radiation; and
   receiving light from the unknown rock sample using a light return waveguide in at least a section of the electromagnetic spectrum ranging from the ultraviolet to the long terahertz radiation.

13. The non-transitory, computer-readable medium of claim 12, the operations further using a rotating/movable attenuated total reflectance (ATR) crystal.

14. The non-transitory, computer-readable medium of claim 8, wherein the predetermined threshold is a 10% change or less.

15. A computer-implemented system, comprising:
   one or more processors; and
   a non-transitory computer-readable storage medium coupled to the one or more processors and storing programming instructions for execution by the one or more processors, the programming instructions instructing the one or more processors to perform operations comprising:
      determining rock and oil electromagnetic baselines of rock samples in at least a section of an electromagnetic spectrum ranging from ultraviolet to long terahertz radiation;
      conducting an aging process on each rock sample, initially starting with the rock and oil electromagnetic baselines;

repeating the aging process using spectrometry on the rock sample and measured wettabilities of the rock sample until changes in spectra are less than a predetermined threshold;

storing aging information, including the spectra and wettabilities, in a machine learning database;

obtaining spectra from an unknown rock sample;

mapping the spectra to clusters in the machine learning database; and determining wettability ranges for the unknown rock sample based on a mapping of the spectra of the unknown rock sample to clusters in the machine learning database.

16. The computer-implemented system of claim 15, wherein the unknown rock sample is a sliding/moving rock sample.

17. The computer-implemented system of claim 15, wherein obtaining the spectra from the unknown rock sample includes integrating sphere/optics providing an light output in at least a section of the electromagnetic spectrum ranging from the ultraviolet to the long terahertz radiation.

18. The computer-implemented system of claim 17, wherein obtaining the spectra from the unknown rock sample includes processing a diffuse reflection from the unknown rock sample.

19. The computer-implemented system of claim 15, wherein obtaining the spectra from the unknown rock sample includes:

sending a light output to the unknown rock sample using a light output waveguide in at least a section of the electromagnetic spectrum ranging from the ultraviolet to the long terahertz radiation; and receiving light from the unknown rock sample using a light return waveguide in at least a section of the electromagnetic spectrum ranging from the ultraviolet to the long terahertz radiation.

20. The computer-implemented system of claim 19, the operations further using a rotating/movable attenuated total reflectance (ATR) crystal.

* * * * *